United States Patent [19]

Asjes, Jr.

[11] Patent Number: Plant 6,539

[45] Date of Patent: Jan. 17, 1989

[54] PYRAMIDAL ENGLISH OAK NAMED ASJES *QUERCUS ROBUR*

[76] Inventor: Evert Asjes, Jr., 11601 Blue River Rd., Kansas City, Mo. 64131

[21] Appl. No.: 940,417

[22] Filed: Dec. 11, 1986

[51] Int. Cl.[4] ..... A01H 5/00

[52] U.S. Cl. ..... Plt./51

[58] Field of Search ..... Plt./51

[56] References Cited

PUBLICATIONS

Trees for American Gardens, Wyman, 1965, Macmillan Publ. Co., N.Y., pp. 408–410.

The Standard Cyclopedia of Horticulture, 1935, Bailey, Macmillan, N.Y. p. 2888.

*Primary Examiner*—Robert E. Bagwill

*Attorney, Agent, or Firm*—Charles W. Rummler

[57] ABSTRACT

A new variety of *Quercus robur* var. fastigiata, particularly characterized by its broad columnar body formation for about one-half of its height with the upper portion tapering inwardly in a fastigiate manner and having closely spaced, narrow branching requiring very little trimming to keep a six to one fastigate growth habit, and being thickly clothed with dark green obovate leaves which have about three to seven rounded lobes on each side, thereby providing a very unusual and excellent form for use as a landscape tree; this new English oak cultivar being especially distinguished by its resistance to mildew on its foliage.

1 Drawing Sheet

BACKGROUND OF THE NEW TREE

This new variety of English oak, *Quercus robur,* var. fastigiata was discovered by me as a seedling variance of this family of English oak trees being grown in my nursery at Kansas City, Mo., and as the seedlings were grown and observed from year to year, this particularly seedling was noted to have characteristics quite different than the others grown in my nursery and because I believed that I had found something quite different and worthwhile, I propagated this particular seedling at Kansas City, Mo., by means of cuttings and buds, as well as by grafting, and I thereby found that the progeny of this original seedling retained the same unusual characteristics of the parent plant from generation to generation; and I also found, from more than ten years of careful observation, that this new tree has, the special characteristic of never having mildew on its foliage, mildew being an inherent disease very prevalent in English oaks.

My new pyramidal English oak variety is also being grown and propagated by budding at Portland, Oreg., and it has been found there that this new English oak variety retains all of the advantageous characteristics of those grown in my nursery at Kansas City, Mo.

DESCRIPTION OF THE DRAWING

My new pyramidal variety of English oak tree is illustrated by the accompanying drawing on which the left hand view shows the discovery tree at a height of about thirty feet and the right hand view shows the same tree pictured more closely to better illustrate its branching and body form nature.

DESCRIPTION OF THE NEW TREE

The following is a description of my new English oak tree cultivar based upon observations of the discovery plant and its propagated clones, the observations having been made at my nursery at Kansas City, Mo.

Origin: Seedling variant.

Parentage: A common English oak variety growing in my nursery at Kansas City, Mo.

Classification:

*Botanic.*—*Quercus robur* var. fastigiata.

*Commercial.*—Pyramidal English Oak.

Form: Generally fastigiate and densely clothed.

Growth rate: Fairly rapid.

Strength: Very strong.

Branching: Numerous, narrow and closely spaced.

Height: The original plant is about thirty feet tall at about ten years.

*Trunk size.*—About 10 inches.

Bark:

*Color.*—Gray brown.

Leaves:

*Quantity.*—Abundant, alternate and auriculate.

*Form.*—Obovate with three to about seven pairs of rounded lobes.

*Size.*—About 4 to 5 inches long and about 3 inches wide.

*Texture.*—Leathery.

*Aspect.*—Glossy.

*Color.*—Both upper and under sides, glaborous dark green, almost holly-like.

Fruit: An elongated acorn, about two inches long with about one-third in the cup.

*Peduncle length.*—About 3 inches.

*Fertility.*—The fruit is fertile.

Effect of weather: This cultivar is extremely hardy and withstands very well the severe midwestern climate.

Disease resistance: This plant has a very strong resistance to mildew, as determined by more than ten years of continuous observation in Kansas City, Mo., and subsequently at Portland, Oreg.

My new pyramidal English oak tree variety grows fairly rapidly and propagates well by budding on seedlings of *Quercus robur* and the new variety seems to be quite compatible in that union. Its general physical characteristics are similar to those of the parent tree, including both foliage and acorns, its particular distinction, however, being that the new cultivar appears to be completely free of mildew.

I claim:

1. A new and distinct variety of *Quercus robur* var. fastigiata and the parts thereof, substantially as herein shown and described, and being particularly distinguished by its fast growing, densely clothed fastigiate form and its very strong resistance to mildew.

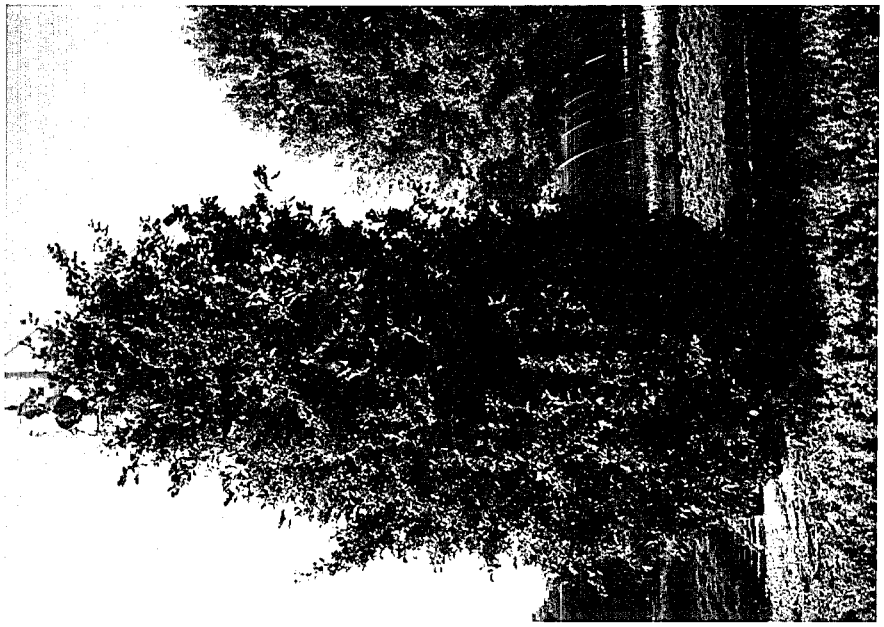
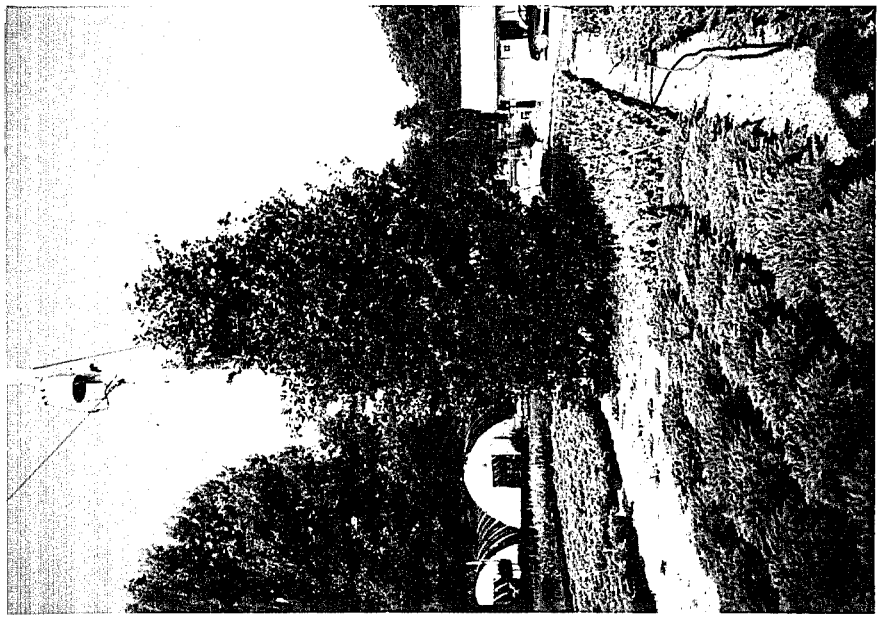

* * * * *